US009623094B2

(12) United States Patent
Harel et al.

(10) Patent No.: US 9,623,094 B2
(45) Date of Patent: Apr. 18, 2017

(54) MICROPARTICULATED VACCINES FOR THE ORAL OR NASAL VACCINATION AND BOOSTERING OF ANIMALS INCLUDING FISH

(75) Inventors: Moti Harel, Pikesville, MD (US); Brian Carpenter, Baltimore, MD (US)

(73) Assignee: Advanced BioNutrition Corporation, Columbia, MD (US)

( * ) Notice: Subject to any disclaimer, the term of this patent is extended or adjusted under 35 U.S.C. 154(b) by 0 days.

(21) Appl. No.: 13/260,661

(22) PCT Filed: Mar. 26, 2010

(86) PCT No.: PCT/US2010/028767
§ 371 (c)(1),
(2), (4) Date: Nov. 2, 2011

(87) PCT Pub. No.: WO2010/111565
PCT Pub. Date: Sep. 30, 2010

(65) Prior Publication Data
US 2012/0040010 A1     Feb. 16, 2012

Related U.S. Application Data

(60) Provisional application No. 61/163,910, filed on Mar. 27, 2009, provisional application No. 61/294,672, filed on Jan. 13, 2010.

(51) Int. Cl.
A61K 39/12      (2006.01)
A61K 39/02      (2006.01)
(Continued)

(52) U.S. Cl.
CPC .............. *A61K 39/00* (2013.01); *A61K 9/006* (2013.01); *A61K 9/0043* (2013.01);
(Continued)

(58) Field of Classification Search
None
See application file for complete search history.

(56) References Cited

U.S. PATENT DOCUMENTS 3,241,977 A    3/1966  Mitchell
3,897,307 A    7/1975  Porubcan
(Continued)

FOREIGN PATENT DOCUMENTS

CA    2807997    2/2012
CL    931-2008   3/2008
(Continued)

OTHER PUBLICATIONS

Li et al., Preparation of alginate coated chitosan microparticles for vaccine delivery, BMC Biotechnology 8:89 (2008).*
(Continued)

*Primary Examiner* — Bethany Barham
*Assistant Examiner* — Dominic Lazaro
(74) *Attorney, Agent, or Firm* — Ratnerprestia

(57) ABSTRACT

The invention relates to a composition and a method for manufacturing semi-dry or dry particles containing a mucoadhesive polymer and a bioactive agent such as, but not limited to, an Immunogenic Substance (e.g., a vaccine), that allows the oral or nasal administration and delivery of the bioactive agent essentially unaltered to mucosal surfaces in the animal, including an aquatic animal.

22 Claims, 3 Drawing Sheets

(51) Int. Cl.

| | |
|---|---|
| *A61P 31/14* | (2006.01) |
| *A61K 47/36* | (2006.01) |
| *A61K 9/14* | (2006.01) |
| *A61P 31/00* | (2006.01) |
| *A61K 47/30* | (2006.01) |
| *A61K 39/00* | (2006.01) |
| *A61K 9/00* | (2006.01) |
| *A61K 39/145* | (2006.01) |

(52) U.S. Cl.
CPC ...... *A61K 39/0208* (2013.01); *A61K 39/0233* (2013.01); *A61K 39/0241* (2013.01); *A61K 39/12* (2013.01); *A61K 39/145* (2013.01); *A61K 2039/522* (2013.01); *A61K 2039/5258* (2013.01); *A61K 2039/541* (2013.01); *A61K 2039/542* (2013.01); *A61K 2039/543* (2013.01); *A61K 2039/552* (2013.01); *A61K 2039/55555* (2013.01); *A61K 2039/55583* (2013.01); *C12N 2720/10011* (2013.01); *C12N 2720/10034* (2013.01); *C12N 2740/10011* (2013.01); *C12N 2740/10034* (2013.01); *C12N 2760/10034* (2013.01); *C12N 2760/16011* (2013.01); *C12N 2760/16034* (2013.01)

(56) References Cited

U.S. PATENT DOCUMENTS

| | | |
|---|---|---|
| 4,337,242 A | 6/1982 | Markus |
| 4,656,767 A | 4/1987 | Tarrant |
| 5,227,373 A | 7/1993 | Alexander |
| 5,262,187 A | 11/1993 | Hahn |
| 5,407,957 A | 4/1995 | Kyle |
| 5,518,918 A | 5/1996 | Barclay |
| 5,637,494 A | 6/1997 | King |
| 5,658,767 A | 8/1997 | Kyle |
| 5,715,774 A | 2/1998 | Adey |
| 5,731,006 A | 3/1998 | Akiyama |
| 5,766,520 A | 6/1998 | Bronshtein |
| 5,908,622 A | 6/1999 | Barclay |
| 5,958,455 A | 9/1999 | Roser |
| 5,968,569 A | 10/1999 | Cavadini |
| 5,981,719 A | 11/1999 | Woiszwillo |
| 6,060,050 A | 5/2000 | Brown |
| 6,187,330 B1 | 2/2001 | Wang |
| 6,190,701 B1 | 2/2001 | Roser |
| 6,258,362 B1 | 7/2001 | Loudon |
| 6,267,958 B1 | 7/2001 | Andya |
| 6,290,991 B1 | 9/2001 | Roser |
| 6,306,345 B1 | 10/2001 | Bronshtein |
| 6,331,310 B1 | 12/2001 | Roser |
| 6,338,856 B1 | 1/2002 | Allen |
| 6,338,866 B1 | 1/2002 | Criggall |
| 6,451,567 B1 | 9/2002 | Barclay |
| 6,468,782 B1 | 10/2002 | Tunnacliffe |
| 6,503,411 B1 | 1/2003 | Franks |
| 6,509,146 B1 | 1/2003 | Bronshtein |
| 6,509,178 B1 | 1/2003 | Tanaka |
| 6,534,087 B2 | 3/2003 | Busson |
| 6,537,666 B1 | 3/2003 | Bronshtein |
| 6,565,871 B2 | 5/2003 | Roser |
| 6,582,941 B1 | 6/2003 | Yokochi |
| 6,586,006 B2 | 7/2003 | Roser |
| 6,589,560 B2 | 7/2003 | Foster |
| 6,664,099 B1 | 12/2003 | Worrall |
| 6,716,460 B2 | 4/2004 | Abril |
| 6,726,934 B1 | 4/2004 | Prokop |
| 6,733,759 B2 | 5/2004 | Ivey |
| 6,790,453 B2 | 9/2004 | Porzio |
| 6,797,266 B2 | 9/2004 | Naidu |
| 6,811,792 B2 | 11/2004 | Roser |
| 6,841,181 B2 | 1/2005 | Jager |
| 6,872,357 B1 | 3/2005 | Bronshtein |
| 6,884,866 B2 | 4/2005 | Bronshtein |
| 6,900,173 B2 | 5/2005 | Martin |
| 6,919,172 B2 | 7/2005 | DePablo |
| 6,964,771 B1 | 11/2005 | Roser |
| 7,005,280 B2 | 2/2006 | Barclay |
| 7,052,719 B2 | 5/2006 | Bernstein |
| 7,056,495 B2 | 6/2006 | Roser |
| 7,122,370 B2 | 10/2006 | Porubcan |
| 7,153,472 B1 | 12/2006 | Bronshtein |
| 7,258,873 B2 | 8/2007 | Truong-Le |
| 7,282,194 B2 | 10/2007 | Sung |
| 7,381,425 B1 | 6/2008 | Truong-Le |
| 7,396,548 B2 | 7/2008 | Kyle |
| 7,744,925 B2 | 6/2010 | Roser |
| 7,842,310 B2 | 11/2010 | Hwang |
| 7,927,858 B2 | 4/2011 | Mayeresse |
| 7,939,105 B2 | 5/2011 | Parikh |
| 7,998,502 B2 | 8/2011 | Harel |
| 8,097,245 B2 | 1/2012 | Harel |
| 8,377,496 B2 | 2/2013 | Clinger |
| 8,460,726 B2 | 6/2013 | Harel |
| 8,834,951 B2 | 9/2014 | Harel |
| 8,968,721 B2 | 3/2015 | Harel |
| 9,044,497 B2 | 6/2015 | Harel |
| 9,072,310 B2 | 7/2015 | Harel |
| 2001/0012610 A1 | 8/2001 | Bronshtein |
| 2001/0016220 A1 | 8/2001 | Jager |
| 2002/0192202 A1 | 12/2002 | Naidu |
| 2003/0017192 A1 | 1/2003 | Kanafani |
| 2003/0022333 A1 | 1/2003 | Bronshtein |
| 2003/0165472 A1 | 9/2003 | McGrath |
| 2003/0190332 A1* | 10/2003 | Gilad et al. ............... 424/227.1 |
| 2004/0038825 A1 | 2/2004 | Leland |
| 2004/0047881 A1 | 3/2004 | Kyle |
| 2004/0081638 A1 | 4/2004 | Kyle |
| 2004/0081699 A1 | 4/2004 | Rademacher |
| 2004/0175389 A1 | 9/2004 | Porubcan |
| 2004/0177392 A1 | 9/2004 | Barratt |
| 2004/0219206 A1 | 11/2004 | Roser |
| 2004/0241313 A1 | 12/2004 | Nana |
| 2005/0019417 A1 | 1/2005 | Ko |
| 2005/0032192 A1 | 2/2005 | Vesey |
| 2005/0079244 A1 | 4/2005 | Giffard |
| 2005/0100559 A1 | 5/2005 | Myatt |
| 2005/0153018 A1 | 7/2005 | Ubbink |
| 2005/0241011 A1 | 10/2005 | Allnut |
| 2005/0266069 A1 | 12/2005 | Simmons |
| 2006/0008861 A1 | 1/2006 | Allnutt |
| 2006/0024404 A1 | 2/2006 | Kyle |
| 2006/0120999 A1 | 6/2006 | Dhar |
| 2006/0121468 A1 | 6/2006 | Allnutt |
| 2006/0127453 A1 | 6/2006 | Harel |
| 2006/0130162 A1 | 6/2006 | Kyle |
| 2006/0147500 A1 | 7/2006 | Klingeberg |
| 2006/0154067 A1 | 7/2006 | Cooper |
| 2006/0222694 A1 | 10/2006 | Oh |
| 2006/0258623 A1 | 11/2006 | Harel |
| 2006/0265766 A1 | 11/2006 | Kyle |
| 2007/0020289 A1 | 1/2007 | Mattern |
| 2007/0031534 A1 | 2/2007 | Tsujimoto |
| 2007/0082008 A1 | 4/2007 | Harel |
| 2007/0122397 A1 | 5/2007 | Sanguansri |
| 2007/0207165 A1* | 9/2007 | Thiry et al. ............... 424/190.1 |
| 2007/0292952 A1 | 12/2007 | Dhar |
| 2008/0044081 A1 | 2/2008 | Lieb |
| 2008/0044481 A1 | 2/2008 | Harel |
| 2008/0050497 A1 | 2/2008 | Mai |
| 2008/0102132 A2 | 5/2008 | Giner |
| 2008/0131514 A1 | 6/2008 | Truong-Le |
| 2008/0193546 A1 | 8/2008 | Roser |
| 2008/0194504 A1 | 8/2008 | Kyle |
| 2008/0221231 A1 | 9/2008 | Cooper |
| 2008/0229609 A1 | 9/2008 | Bronshtein |
| 2008/0241244 A1 | 10/2008 | Truong-Le |
| 2008/0261916 A1 | 10/2008 | Jaszberenyi |
| 2009/0155351 A1 | 6/2009 | Hejl |
| 2009/0162518 A1 | 6/2009 | Clinger |
| 2009/0162521 A1 | 6/2009 | Clinger |
| 2009/0181363 A1 | 7/2009 | Dhar |
| 2009/0203592 A1 | 8/2009 | Beermann |

(56) References Cited

U.S. PATENT DOCUMENTS

| | | |
|---|---|---|
| 2009/0208585 A1 | 8/2009 | Roser |
| 2009/0232894 A1 | 9/2009 | Chouvenc |
| 2009/0238890 A1 | 9/2009 | Piechocki |
| 2009/0246184 A1 | 10/2009 | Harel |
| 2009/0324636 A1 | 12/2009 | Piechocki |
| 2010/0015177 A1 | 1/2010 | Drew |
| 2010/0047393 A1 | 2/2010 | Glas |
| 2010/0074994 A1 | 3/2010 | Harel |
| 2010/0086638 A1 | 4/2010 | Kyle |
| 2010/0092521 A1 | 4/2010 | Dhar |
| 2010/0120014 A1 | 5/2010 | Bronshtein |
| 2010/0120676 A1 | 5/2010 | Boehm |
| 2010/0189767 A1 | 7/2010 | Shimoni |
| 2010/0242301 A1 | 9/2010 | Rampersad |
| 2010/0297231 A1 | 11/2010 | Vehring |
| 2011/0070334 A1 | 3/2011 | Rangavajla |
| 2011/0223282 A1 | 9/2011 | BergonzelliDegonda |
| 2012/0009248 A1 | 1/2012 | Truong-Le |
| 2012/0039956 A1 | 2/2012 | Harel |
| 2012/0040010 A1 | 2/2012 | Harel |
| 2012/0114621 A1 | 5/2012 | Harel |
| 2012/0135017 A1 | 5/2012 | Harel |
| 2012/0288483 A1 | 11/2012 | Harel |
| 2012/0322663 A1 | 12/2012 | Harel |
| 2013/0287896 A1 | 10/2013 | Harel |
| 2013/0296165 A1 | 11/2013 | Harel |

FOREIGN PATENT DOCUMENTS

| | | |
|---|---|---|
| CN | 101287449 | 10/2008 |
| CN | 101951789 | 1/2011 |
| CN | 102186360 | 9/2011 |
| EP | 0028563 | 5/1981 |
| EP | 0259739 | 3/1988 |
| EP | 0471904 | 2/1992 |
| EP | 1110462 | 6/2001 |
| EP | 1344458 | 9/2003 |
| GB | 1232057 | 5/1971 |
| GB | 2389787 | 12/2003 |
| JP | 57114527 | 7/1982 |
| JP | 05246856 | 9/1993 |
| JP | 06022746 | 2/1994 |
| JP | 11506467 | 6/1999 |
| JP | 11513700 | 11/1999 |
| JP | 2001505431 | 4/2001 |
| JP | 2002512970 | 5/2002 |
| JP | 2002530321 | 9/2002 |
| JP | 2004506437 | 3/2004 |
| JP | 2004525106 | 8/2004 |
| JP | 2004528288 | 9/2004 |
| JP | 2005501268 | 1/2005 |
| JP | 2005519600 | 7/2005 |
| JP | 2005270100 | 10/2005 |
| JP | 2005534741 | 11/2005 |
| JP | 2007519796 | 7/2007 |
| JP | 2007522085 | 8/2007 |
| JP | 2009522280 | 6/2009 |
| JP | 2010512755 | 4/2010 |
| KR | 20050105669 | 11/2005 |
| KR | 1020050106559 | 11/2005 |
| WO | 9527721 | 10/1995 |
| WO | 9640077 | 12/1996 |
| WO | 9824327 | 6/1998 |
| WO | 9824882 | 6/1998 |
| WO | WO 00 32064 * | 8/2000 |
| WO | 0112779 | 2/2001 |
| WO | 0136590 | 5/2001 |
| WO | 0215720 | 2/2002 |
| WO | 02058735 | 8/2002 |
| WO | 02061111 | 8/2002 |
| WO | 02076391 | 10/2002 |
| WO | 03086454 | 10/2003 |
| WO | 03088755 | 10/2003 |
| WO | 03089579 | 10/2003 |
| WO | 03103692 | 12/2003 |
| WO | 2004022728 | 3/2004 |
| WO | 2004024177 | 3/2004 |
| WO | 2004039417 | 5/2004 |
| WO | 2004043139 | 5/2004 |
| WO | 2004080196 | 9/2004 |
| WO | 2004091307 | 10/2004 |
| WO | 2004112767 | 12/2004 |
| WO | 2004112776 | 12/2004 |
| WO | 2005030229 | 4/2005 |
| WO | 2005060937 | 7/2005 |
| WO | 2005084646 | 9/2005 |
| WO | 2005105978 | 11/2005 |
| WO | 2005117962 | 12/2005 |
| WO | WO 2005115341 A2 * | 12/2005 |
| WO | WO 2006085082 A1 * | 8/2006 |
| WO | 2006122299 | 11/2006 |
| WO | 2007035455 | 3/2007 |
| WO | 2007038926 | 4/2007 |
| WO | 2007067207 | 6/2007 |
| WO | 2007075988 | 7/2007 |
| WO | 2007084059 | 7/2007 |
| WO | 2007084500 | 7/2007 |
| WO | WO2007/079147 | 7/2007 |
| WO | WO 2007079147 A2 * | 7/2007 |
| WO | 2007117511 | 10/2007 |
| WO | 2007136553 | 11/2007 |
| WO | 2008016214 | 2/2008 |
| WO | 2008056983 | 5/2008 |
| WO | 2008076975 | 6/2008 |
| WO | 2009002481 | 12/2008 |
| WO | 2009140327 | 11/2009 |
| WO | 2010002418 | 1/2010 |
| WO | 2010046321 | 4/2010 |
| WO | 2010111347 | 9/2010 |
| WO | 2010118188 | 10/2010 |
| WO | 2010118205 | 10/2010 |
| WO | 2010135495 | 11/2010 |
| WO | 2010138522 | 12/2010 |
| WO | 2011094469 | 8/2011 |

OTHER PUBLICATIONS

Li (Li et al., Preparation of alginate coated chitosan microparticles for vaccine delivery, BMC Biotechnology 8:89 (2008); on Nov. 8, 2012 IDS).*

International Search Report for Application No. PCT/US2010/028767 dated Dec. 23, 2010.

Examination Report on Patent Application for Chilean Application No. 759-09.

Aral, C. et al., "Alternative approach to the preparation of chitosan beads," International Journal of Pharmaceutics 168 (1998) 9-15.

Bradford, M., "A rapid and sensitive method for the quantitation of microgram quantities of protein utilizing the principle of protein-dye binding," Analytical biochemistry 72 (1976) 248-254.

Bodmeier, R., et al., "Preparation and evaluation of drug-containing chitosan beads," Drug Development and Industrial Pharmacy, 15 (1989) 1475-1494.

Calvo, P., et al., "Novel hydrophilic chitosan-polyethylene oxide nanoparticles as protein carriers," Journal of Applied Polymer Science, 63 (1997) 125-132.

Chopra, S., et al., "Advances and potential applications of chitosan derivatives as mucoadhesive biomaterials in modern drug delivery," Journal of Pharmacy and Pharmacology, 58 (2006) 1021-1032.

Dang, J., et al., "Natural polymers for gene delivery and tissue engineering," Advanced Drug Delivery Reviews, 58 (2006) 487-499.

Davis, S., "The use of soluble polymers and polymer microparticles to provide improved vaccine responses after parenteral and mucosal delivery," Vaccine, 24S2 (2006) 7-10.

Huang, Y.-C., et al., "Optimizing formulation factors in preparing chitosan microparticles by spray-drying method," Journal of Microencapsulation, 20 (2003) 247-260.

Kang, M., et al., "Pluronic F127 enhances the effect as an adjuvant of chitosan microspheres in the intranasal delivery of bordetella bronchiseptica antigens containing dermonec

(56) References Cited

OTHER PUBLICATIONS

Kim, T., et al., "Stimulation of mucosal and systemic antibody responses against recombinant transferrin-binding protein b of actinobacillus pleuropneumoniae with chitosan after tracheal administration in piglets," Journal of Veterinary Medical Science, 69 (2007) 535-539.

Li, X., et al., "Preparation of alginate coated chitosan microparticles for vaccine delivery," BMC Biotechnology 8:89 (2008).

Malik, D., et al., "Recent advances I protein and peptide drug delivery systems," Current Drug Delivery, 4 (2007) 141-151.

Panos, I., et al., "New drug delivery systems based on chitosan," Current Drug Discovery Technologies, 5 (2008) 333-341.

Rege, P., et al., "Spray-dried chitinosans Part I: preparation and characterization," International Journal of Pharmaceutics 252 (2003) 41-51.

Shiraishi, S., et al., "Controlled release of indomethacin by chitosan-polyelectrolyte complex: optimization and in vivo/in vitro evaluation," Journal of Controlled Release 25 (1993) 217-225.

Shu, X., et al., "A novel approach to prepare tripolyphosphate/chitosan complex beads for controlled release drug delivery," International Journal of Pharmaceutics 201 (2000) 51-58.

Van der Lubben, I.M., et al., "Chitosan for mucosal vaccination," Advanced Drug Delivery Reviews 52(2001) 139-144.

Van der Lubben, I.M., et al., "Chitosan microparticles for oral vaccination: preparation, characterization and preliminary in vivo uptake studies in murine Peyer's patches," Biomaterials 22 (2001) 687-694.

Zhou, S., et al., "Poly-D,L-lactide-co-poly(ethylene glycol) microspheres as potential vaccine delivery systems," Journal of Controlled Release 86 (2003) 195-205.

Tobar et al., Oral Vaccination of Atlantic Salmon Salmo salar against Salmonid rickettsial septicaemia (SRS), abstract, World Aquaculture Society's 2008 annual international conference (May 19-23, 2008).

Tobar et al., Oral Vaccination of Atlantic Salmon Salmo salar against Salmon Rickettsial Septicaemia, presentation, World Aquaculture Society's 2008 annual international conference (May 19-23, 2008).

Canadian Office Action dated Mar. 10, 2016 for Canadian Application No. 2,763,074.

Chinese Office Action dated Feb. 26, 2016 for Chinese Application No. 201380015928.0 with translation.

Chinese Search Report dated Feb. 23, 2016 for Chinese Application No. 2013800115928.0 with translation.

Chinese Office Action dated Apr. 1, 2016 for Chinese Application No. 201410326898.1 with translation.

Philippines Substantive Examination Report dated Apr. 15, 2016 for Philippines Application No. 1-2012-501410.

Non Final Office Action dated Jan. 22, 2016 for U.S. Appl. No. 13/321,708.

Non Final Office Action mailed Feb. 3, 2016 for U.S. Appl. No. 14/456,130.

Final Office Action mailed Feb. 3, 2016 for U.S. Appl. No. 13/849,941.

Philippine Office Action dated Jan. 14, 2016 for Philippine Application No. 1-2011-502445.

Non Final Office Action mailed Jan. 12, 2016 for U.S. Appl. No. 14/479,791.

Canadian Office Action mailed Dec. 8, 2015 for Canadian Application No. 2,756,883.

Chinese Reexamination Report dated Dec. 23, 2015 for Chinese Application No. 201080029392.4 with translation.

Abdelwahed et al., Advanced Drug Delivery Reviews, 58:1688-1713 (2006).

Anal et al., "Recent advances in microencapsulation of probiotics for industrial applications and targeted delivery." Trends in Food Science and Technology, vol. 18, No. 5, Apr. 29, 2007, pp. 240-251.

Anderson, J.W., Johnstone, B.M. and Remley, D.T. (1999). Breast-feeding and cognitive development: a meta-analysis. Am J Clin Nutr, 70, 525-35.

Annear, D., "The preservation of leptospires by drying from the liquid state," Journal of General Microbiology, 27 (1962) 341-343.

Australian Patent Examination Report dated Jan. 23, 2015 in Patent Application No. 2010254235.

Bazan, N.G. and Rodriguez de Turco E.B. (1994). Review: pharmacological manipulation of docosahexaenoic-phospholipid biosynthesis in photoreceptor cells: implications in retinal degeneration. J. Ocul Pharmacol, 10, 591-604.

Bazan, N.G. and Scott, B.L. (1990). Dietary omega-3 fatty acids and accumulation of docosahexaenoic acid in rod photoreceptor cells of the retina and synapses. Ups J Med Sci Suppl, 48, 97-107.

Behrens, P. and Kyle, D. (1996). Microalgae as a source of fatty acids, J Food Sci, 3, 259-272.

Benedict, R.G. et al., "Preservation of Microorganisms by Freeze-Drying I. Cell Supernatant Naylor-Smith Solution, and Salts of Various Acids as Stabilizers for Serratia marcascens," Appl. Microbiol, 1958, vol. 6, No. 6, pp. 401-407.

Bergogne et al. Molecular Crystals and Liquid Crystals, 354: 79-89 (2000).

Boswell KDB, Gladue R, Prima B, Kyle DJ (1992) SCO production of fermentive microalgae. In: Kyle DJ, Ratledge C (eds) Industrial Applications of Single Cell Oils. American Oil Chemists Society, Champaign, IL., pp. 274-286.

Canadian Office Action mailed Apr. 6, 2011 in Canadian Application No. 2,673,120.

Canadian Office Action mailed Oct. 10, 2014 in Canadian Application No. 2,785,815.

Canadian Office Action mailed Sep. 8, 2015 for Canadian Application No. 2,785,815.

Capela, P., et al., "Effect of cryoprotectants, prebiotics and microencasulation on survival of probiotic organisms in yoghurt and freeze-dried yoghurt," Food Research International, 39 (2006) 203-211.

Chen, et al., "Beneficial Effect of Intracellular Trehalose on the Membrane Integrity of Dried Mammalian Cells", Cryobiology vol. 43, pp. 168-181, 2001.

Chen et al., China Tropical Medicine, 7(4):654-55 (2007) (with partial English translation).

Chinese Office Action mailed Mar. 2, 2015 in Chinese Application No. 201180007562.3.

Chinese Search Report dated May 26, 2014 for application No. 201180039219.7 filed Aug. 12, 2011.

Crawford, M.A., Costeloe, K., Ghebremeskel, K. and Phylactos, A. (1998). The inadequacy of the essential fatty acid content of present preterm feeds [published erratum appears in Eur J. Pediatr Feb. 1998;157(2):160]. Eur J Pediatr, 157 Suppl 1, S23-7.

Crowe, J.H., Carpenter, J.F., and Crowe, L.M. (1998). "The role of vitrification in anhydrobiosis." Annu. Rev Physiol. 60:73-103.

Crowe, J.H., Crowe., L.M., and Mouriadian, R., 1983, Cryobiology, 20, 346-356.

Crowe et al., "Anhydrobiosis: A Strategy for Survival", Adv. Space Res vol. 12, No. 4, pp. 239-247, 1992.

De Giulio, et al., "Use of alginate and cryo-protective sugars to improve the viability of lactic acid and bacteria after freezing and freeze-drying", World Journal of Microbiology and Biotechnology, Kluwer Academic Publishers, DO, vol. 21, No. 5, Jul. 1, 2005, pp. 739-746.

Desai et al., Pharmaceutical Research, 13(12):1838-45 (1996).

Entire patent prosecution history of U.S. Appl. No. 12/519,860, filed Dec. 2, 2009, entitled, "Dry Food Product Containing Live Probiotic," now U.S. Pat. No. 8,460,726.

Entire prosecution history of U.S. Appl. No. 12/159,407, filed Nov. 21, 2008, entitled, "Delivery Vehicle for Probiotic Bacteria Comprising a Dry Matrix of Polysaccharides, Saccharides and Polyols in a Glass Form and Methods of Making Same," now U.S. Pat. No. 8,097,245.

Entire prosecution history of U.S. Appl. No. 13/208,459, filed Aug. 12, 2011, entitled, "Dry Storage Stabilizing Composition for Biological Materials."

Entire prosecution history of U.S. Appl. No. 13/321,708, filed Feb. 6, 2012, entitled, "Stable Dry Powder Composition Comprising Biologically Active Microorganisms and/or Bioactive Materials and Methods of Making."

(56) References Cited

OTHER PUBLICATIONS

Entire prosecution history of U.S. Appl. No. 13/351,343, filed Jan. 17, 2012, entitled, "Delivery Vehicle for Probiotic Bacteria Comprising a Dry Matrix of Polysaccharides, Saccharides and Polyols in a Glass Form and Methods of Making Same."
Entire prosecution history of U.S. Appl. No. 13/378,106, filed Mar. 29, 2012, entitled, "Dry Glassy Composition Comprising a Bioactive Material," now U.S. Pat. No. 8,834,951.
Entire prosecution history of U.S. Appl. No. 13/459,408, filed Apr. 30, 2012, entitled, "Delivery Vehicle for Probiotic Bacteria Comprising a Dry Matrix of Polysaccharides, Saccharides and Polyols in a Glass Form and Methods of Making Same."
Entire prosecution history of U.S. Appl. No. 13/849,941, filed Mar. 25, 2013, entitled Stablizing Composition for Biological Materials.
Entire prosecution history of U.S. Appl. No. 13/911,636, filed Jun. 6, 2013, entitled, "Dry Food Product Containing Live Probiotic."
Entire prosecution history of U.S. Appl. No. 14/456,130, filed Aug. 11, 2014, entitled, "Dry Glassy Composition Comprising a Bioactive Material."
Entire prosecution history of U.S. Appl. No. 14/479,791, filed Sep. 8, 2014, entitled, "Dry Food Product Containing Live Probiotic."
Esquisabel et al., 1997, J. Microencapsulation, 14, 627-638.
European Office Action for Application No. 10 781 100.2-1403 dated Oct. 17, 2014.
European Office Action mailed Nov. 6, 2015 for European Application No. 11817090.1.
Extended European Search Report for European Application No. 11817090.1-1358 dated Jun. 16, 2014.
Extended European Search Report for European Application No. 13764138.7-1460 dated Apr. 9, 2015.
Favaro-Trindade et al., "Microencapsulation of L. acidophilus (La-05) and B. lactis (Bb-12) and evaluation of their survival at the pH values of the stomach and in bile", J. Microencapsulation, vol. 19, pp. 485-494, 2002.
First Office Action with a Search Report issued by the State Intellectual Property Office of the Peoples Republic of China on May 22, 2013 for Chinese Application No. 201180007562.3 (with English Translation).
Grinstead G, Tokach M, Dritz S, Goodband R, Nelssen J (2000) Effects of Spirulina platensis on growth performance of weanling pigs. Animal Feed Sci Technol 83:237-247.
He ML, Hollwich W, Rambeck WA (2002) Supplementation of algae to the diet of pigs: a new possibility to improve the iodine content in the meat. J Animal Physiol Animal Nutri 86:97-104.
Hincha, D., et al., "Protection of liposomes against fusion during drying by oligosaccharides is not predicted by the calorimetric glass transition temperatures of the dry sugars," European Biophysics Journal, 37 (2008) 503-508.
Hughes, V.X. and Hillier, S.L. (1990). "Microbiologic characteristics of Lactobacillus products used for colonization of the vagina." Obstet Gynecol. 75:244-248.
Ikemoto, A., Kobayashi, T., Watanabe, S. and Okuyama, H. (1997). Membrane fatty acid modifications of PC12 cells by arachidonate or docosahexaenoate affect neurite outgrowth but not norepinephrine release. Neurochem Res, 22, 671-8.
International Preliminary Report on Patentability and Written Opinion for PCT International Application No. PCT/US2013/033505 issued Sep. 23, 2014.
International Preliminary Report on Patentability for PCT International Application No. PCT/US2011/022821 dated Jul. 31, 2012.
International Search Report for corresponding International Application No. PCT/US2006/49434 dated Sep. 26, 2007.
International Search Report for corresponding International Application No. PCT/US2007/087771 mailed May 16, 2008.
International Search Report for International Application No. PCT/US2010/036098 mailed Feb. 14, 2011.
International Search Report for International Application No. PCT/US2011/022821 mailed Oct. 25, 2011.
Isolauri et al., "Probiotics: effects on immunity", Am J Clin Nutr. 73, pp. 444S-450S, 2001.

Japanese Office Action for Japanese Patent Application No. 2008-548729, mailed Jul. 23, 2012 (with English translation).
Japanese Office Action issued in Japanese Application No. 2013-524242, dated Jan. 21, 2014 (English tranlsation only).
Japanese Office Action issued Mar. 2, 2015 in Japanese Application No. 2012-551295.
Japanese Office Action issued Mar. 31, 2015 in Japanese Application No. 2012-513183.
Japanese Office Action issued Oct. 7, 2015 in Japanese Application No. 2012-551295, including English translation.
Japanese Office Action mailed Aug. 1, 2014 in Japanese Application No. 2012-513183, with translation (with English translation).
Japanese Office Action mailed Sep. 15, 2015 for Japanese Application No. 2012-513183, including English translation.
Kailasapathy et al., "Survival and therapeutic potential of probiotic organisms with reference to Lactobacillus acidophilus and *Bifidobacterium* spp.," Immunology Cell Biology, 78, pp. 80-88, 2000.
Kearney, et al., "Enhancing the Viability of Lactobacillus plantarum Inoculum by Immobilizing the Cells in Calcium-Alginate Beads Incorporation Cryoprotectants", Applied and Environmental Microbiology, vol. 56, No. 10, Oct. 1990, pp. 3112-3116.
Kets et al, "Citrate increases glass transition temperature of vitrified sucrose preparations," Cryobiology 48 (2004), 46-54.
Krallish et al., "Effect of xylitol and trehalose on dry resistance of yeasts", Appl. Microbiol Biotechnol. 47, pp. 447-451, 1997.
Krasaekoopt et al. "Evaluation of encapsulation techniques of probiotics for yoghurt." International Dairy Journal 13, 2003. pp. 3-13.
Liao et al., "Protective Mechanism of Stabilizing Excipients against Dehydration in the Freeze-Drying of Proteins", Pharmaceutical Research, vol. 19, No. 12, pp. 1854-1861, 2002.
Linders et al., "Effect of Added Carbohydrates on Membrane Phase Behavior and Survival of Dried Lactobacillus plantarum", Cryobiology 35, pp. 31-40, 1997.
M. Le Meste, et al., 2002, Glass Transition and Food Technology: A Critical Appraisal, Journal of Food Science, 67:2444-2458.
Maltrin M100 Maltodrexin, 2006, XP055120984, Internet retrieves from the Internet: URL: http://www.tpipremixes.com/productpdfs/Maltodextrin.pdf, retrieved on Jun. 2, 2014.
Marteau et al., "Protection from gastrointestinal diseases with the use of probiotics", Am J Clin Nutr. 73, pp. 430S-436S, 2001.
Martinez, M. (1990). Severe deficiency of docosahexaenoic acid in peroxisomal disorders: a defect of delta 4 desaturation. Neurology, 40, 1292-8.
Mazur et al., Hydration of Sodium Alginate in Aqueous Solution, Macromolecules, (2014) 47: 771-776.
Mexican Office Action mailed Apr. 16, 2015 in Mexican Application No. MX/a/2012/008795.
Mexican Office Action mailed Jul. 20, 2015 in Mexican Application No. MX/a/2012/008795.
Morgan, C., et al., "Preservation of micro-organisms by drying; a review," Journal of Microbiological Methods, 66 (2006) 183-193.
New Zealand Examination Report dated May 18, 2012 in New Zealand Application No. 597053.
New Zealand Office Action mailed Jun. 24, 2015 in New Zealand Application No. 628912.
Niness, Inulin and Olgifructose: What are they?., J. Nutr. 129, 1999, pp. 1402S-1406S.
Non-Final Office Action mailed Oct. 27, 2015 in U.S. Appl. No. 13/208,459.
Notice of Allowance mailed Feb. 9, 2015 in U.S. Appl. No. 13/351,343.
Notice of Allowance mailed Jan. 15, 2015 in U.S. Appl. No. 13/911,636.
Notice of Allowance mailed Oct. 27, 2014 in U.S. Appl. No. 13/459,408.
Office Action dated Mar. 21, 2014 in Russian patent application No. 2011151788/10(077759) (with English translation).
Office Action for Patent Application JP 2009-541634 mailed Jun. 25, 2012 (with English translation).
Office Action mailed Aug. 6, 2014 in corresponding Russian Application No. 2011151788/10(077759).

(56) References Cited

OTHER PUBLICATIONS

Office Action mailed Jan. 14, 2015 in U.S. Appl. No. 13/321,708.
Office Action mailed Jun. 30, 2015 in Vietnamese Application No. 1-2011-03487.
Office Action mailed May 22, 2015 in U.S. Appl. No. 13/849,941.
Office Action mailed Oct. 27, 2014 in U.S. Appl. No. 13/208,459.
Perdigon et al, "Lactic Acid Bacteria and their Effect on the Immune System", Curr Issues Intest Microbiol. 2, pp. 27-42, 2001.
Perry, Stephen F, "Freeze-Drying and Cryopreservation of Bacteria," Molecular Biotechnology, 1998, vol. 9, No. 1, pp. 59-64.
Philippine Substantive Examination Report mailed Mar. 20, 2015 in Philippine Application No. 1/2011/502445.
Qiu et al., "Permeability of the infective juveniles of Steinernema carpocapsae to glycerol during osmotic dehydration and its effect on biochemical adaptation and energy metabolism", Comparative Biochemistry & Physiology, Part B, vol. 125, pp. 411-419, 2000.
Russian Office Action mailed Dec. 18, 2014 in Application No. 2011151788/10(077759).
Russian Office Action mailed Jul. 21, 2015 in Russian Application No. 2013110833/13(016008).
Sanchez et al., 1999, Intl. J. Pharm. 185, 255-266.
Schwab, C., et al., "Influence of oligosaccharides on the viability and membrane properties of lactobacillus reuteri TMW1.106 during freeze-drying," Cryobiology, 55 (2007) 108-114.
Second Office Action issued by the State Intellectual Property Office of the Peoples Republic of China Feb. 8, 2014 in Chinese Application No. 201180007562.3, including a Search Report (with English translation).
Selmer-Olsen, et al., "Survival of Lactobacillus helveticus entrapped in Ca-alginate in relation to water content, storage and rehydration", Journal of Industrial Microbiology & Biotechnology, vol. 23, 1999, pp. 79-85.
Shah, N.P. (2000). "Probiotic bacteria: selective enumeration and survival in dairy foods." Journal of Dairy Science. 83:894-907.
Shin et al., Growth and Viability of Commerical *Bifidobacterium* spp in Skim Milk containing oligosaccharides and Inulin, Journal of Food Science, 2000, vol. 65, No. 5, pp. 884-887.
Singapore Search Report and Written Opinion mailed Sep. 9, 2015 for Application No. 11201405478V.
Stordy, BJ. (1995). Benefit of docosahexaenoic acid supplements to dark adaptation in dyslexics. Lancet, 346 (8971): 385.
Substantive Examination Adverse Report mailed Aug. 29, 2014 in Malaysian Application No. PI 2011005733.
Substantive Examination Adverse Report mailed Jun. 30, 2015 in Malaysian Application No. PI 2011005733.
Substantive Examination Adverse Report mailed Sep. 15, 2015 in Malaysian Application No. PI 2013000306.
Sucrose, Sucrose Structure, Webpage from Virtual Chembook, Elmhurst College, Charles E. Ophardt, c. 2003.
Supplementary European Search Report for European Appln No. 11737688 dated Sep. 18, 2013.
Supplementary European Search report in European Application No. EP 10781100.2-2405 dated Oct. 9, 2012.
Wong, Recent Patents on Drug Delivery & Formation 3:8-25 (2009).
Xu, L.Z., Sanchez, R., Sali, A. and Heintz, N. (1996).Ligand specificity of brain lipid-binding protein. J Biol Chem, 271, 24711-9.
Zarate et al ("Viability and biological properties of probiotic vaginal lactobacilli after lyophilization and refrigerated storage into gelatin capsules," Process Biochemistry 41 (2006), 1779-1785.
Canadian Offic e Action dated Sep. 9, 2016 for Canadian Application No. 2756883, 4 pages.
Tian, J. et al., "Chitosan micropheres as candidate plasmid vaccine carrier for oral immunisation of Japanese flounder (*Paralichthys olivaceus*)" Dec. 15, 2008, pp. 220-229, vol. 126, Nos. 3-4, Veterinary Immunology and Immunopathology.
Kumar, S.R. et al., "Potential use of chitosan nanoparticies for oral delivery of DNA vaccine in Asian sea bass (*Lates calcarifer*) to protect from Vibrio (*Listonella*) anguillarum", Jul. 2008, pp. 47-56, vol. 25, Nos. 1-2, Fish & Shell Immunology.
Final Office Action for U.S. Appl. No. 13/321,708, mailed Aug. 5, 2016, 30 pages.
Non Final Office Action for U.S. Appl. No. 14/644,248, mailed Jul. 15, 2016, 58 pages.
Notice of Allowance for U.S. Appl. No. 13/848,941, mailed Jun. 20, 2016, 16 pages.
Santivarangkna, et al., "Role of Glassy State on Stabilities of /freeze-Dried Probiotics.", Journal of Food Science, vol. 76, No. 8, 2011, pp. 152-156.
Miao, "Effect of disaccharides on survival during storage of freeze dried probiotics.", Dairy Scieince and Technology 88.1, 2008, pp. 19-30.
European Office Action for European Application No. 10756894.1, dated Jun. 22, 2016, 5 pages.
Notification of Reexamination of Chinese Application No. 201080029392.4, dated Jul. 13, 2016, 10 pages.
European Examination Report for EP Application No. 11817090.1, dated Jul. 15, 2016, 6 pages.
Indonesian Examination Report for Indonesian Application No. W00 2013 00512, dated Jun. 30, 2016, 4 pages.
Indonesian Examination Report for Indonesian Application No. W00 201104583, dated Jun. 27, 2016, 4 pages.
Mexican Office Action for Mexican Application No. MX/a/2013/001535, dated Jul. 13, 2016 with translation, 4 pages.
Canadian Office Action for Canadian Application No. 2,785,815, dated Oct. 14, 2016, 3 pages.
Australian Examination Report for Australian Application No. 2013234931, dated Dec. 7, 2016, 4 pages.
Korean Office Action for Korean Application No. 10-2011-7031038, dated Dec. 27, 2016 with translation, 15 pages.

* cited by examiner

MICROPARTICULATED VACCINES FOR THE ORAL OR NASAL VACCINATION AND BOOSTERING OF ANIMALS INCLUDING FISH

CROSS-REFERENCE TO RELATED APPLICATIONS

This application is filed under the provisions of 35 U.S.C. §371 and claims the priority of International Patent Application No. PCT/US2010/028767 filed on Mar. 26, 2010, which in turn claims priority to U.S. Provisional Application No. 61/163,910 filed in the United States Patent and Trademark Office on Mar. 27, 2009 and U.S. Provisional Application No. 61/294,672 filed in the United States Patent and Trademark Office on Jan. 13, 2010 the contents of which are hereby incorporated by reference herein for all purposes

BACKGROUND OF THE INVENTION

Field of the Invention

The present invention relates generally to encapsulated vaccines and methods of making same, and more particularly, to oral vaccines that release an embedded bioactive agent at the site of action along the foregut and hindgut of an animal and the vaccine is embedded in a cross-linked matrix that is protected by a glassy matrix of sugars.

Related Background Art

Many therapeutic agents, particularly vaccines, are mostly delivered through the injectable route, which is traumatic, inconvenient, expensive, and may fail to induce an appropriate immunogenic response in the mucosal tissues of the animal. In fact, most infections begin at the mucosal surfaces, so immunization against these infective agents depends on the successful induction of a mucosal immune response. While parenteral vaccination is effective at eliciting a systemic immunity, oral vaccines can elicit mucosal immunity and also induce systemic immunity by induction of circulatory antibodies. Oral vaccines are also easier to administer and are less expensive to manufacture than conventional vaccines. However, orally delivered bacterins or subunit vaccines have not been proven to be efficacious since the antigens are generally digested or modified by the stomach prior to presentation to the immuno-responsive cells of the gut mucosa. It is recognized that on passage through the stomach, the vaccine antigenic component(s) can be rapidly inactivated by the gastric pH and digestive enzymes, and thus effective systemic assimilation is compromised. A number of approaches have been tested to provide an oral delivery vehicle that would transit the stomach, but most have been unsuccessful at the commercial scale.

Polymer microspheres and lamellar particles (e.g., liposomes) can be employed for mucosal administration of antigens. Because vaccines themselves may not be efficiently recognized and taken up by mucosal lymphocytes, they typically need to be co-administered with penetration enhancers or adjuvants. Different classes of polymer mixtures are known for potential use as mucoadhesives (Malik, Baboota et al. 2007). These include synthetic polymers such as poly (acrylic acid) (PAA), hydroxypropyl methylcellulose and poly-(methylacrylate) derivatives, as well as naturally occurring polymers such as hyaluronic acid and chitosan. Chitosan has been extensively used for a variety of applications as a biomaterial for tissue engineering, wound healing, and as an excipient for drug delivery (Chopra, Mandi et al. 2006; Dang and Leong 2006). Chitosan has occasionally been tested as an adjuvant for mucosal application (Kim, Kim et al. 2007), but it is typically applied directly to a mucosal surface such as intranasal application in order to obtain IgA response in the nasopharyngeal mucosa of terrestrial animals (Kang, Jiang et al. 2007). Chitosan has also been shown to possess useful properties such as non-toxicity, high biocompatibility and non-antigenicity.

Chitosan can be obtained through the deacetylation of chitin, the major compound of exoskeletons in crustaceans. Chitosan [a-(1~4)-2-amino-2-deoxy-β-D-glucan], a mucopolysaccharide closely related to cellulose, exhibits chemical properties that are determined by the molecular weight, degree of deacetylation, and viscosity. Chitosan can form microparticles and nanoparticles that can encapsulate large amounts of antigens (van der Lubben, Verhoef et al. 2001; Davis 2006). In the acidic environment of the stomach, chitosan retains its positive charges that hold the particle together. It has been shown that ovalbumin loaded chitosan microparticles can be taken up by the Peyer's Patches of the gut associated lymphoid tissue of higher vertebrates. Additionally, after co-administering chitosan with antigens in nasal vaccination studies, a strong enhancement of both mucosal and systemic immune responses in mice was observed (van der Lubben, Verhoef et al. 2001).

As a result of its interesting properties, chitosan has become the subject of numerous scientific reports and patents on the preparation of microspheres and microcapsules. Chitin and chitosan are being extensively used in the pharmaceutical industry (cosmetics, contact lenses, artificial skin, wound dressing), paper making, photography, solid state batteries, waste water treatment, chromatography, dietary supplements and animal feed. Processing techniques for the preparation of chitosan microspheres have been extensively developed since the 1980s. Several processing approaches have been proposed including ionotropic gelation with an oppositely charged, simple or complex coacervation, emulsification/solvent evaporation and, more recently, spray drying (Huang et al. 2003). Chitosan microspheres obtained by spray drying are characterized by high sphericity and specific surface area, which are important parameters for application in the pharmaceutical field (Rege, 2003).

One particular advantage of chitosan is its ability to form a gel matrix with counter-ions such as sodium tripolyphosphate (TPP) (Bodmeier et al. 1989, Shiraishi et al. 1993, Calvo et al. 1997). TPP is a non-toxic and multivalent anion. It can form either intermolecular or intramolecular links between positively charged amino groups of chitosan and negatively charged counter-ion of TPP (Aral and Akbuga 1998; Shu and Zhu 2000).

Against this background, there is a need for an attractive composition and manufacturing method for an oral delivery system that is cost effective, simple to prepare, and also permits prolonged storage stability while maintaining a high loading capacity for the bioactive agent with retention of its in-vivo immunogenicity. Further desirable benefits of the delivery system would include the accurate dosing of bioactive agent, and the ability of stabilizing and protecting the bioactive agent during the manufacturing process itself (e.g. pelleting or extrusion of a food of feed product). It is the objective of the present invention to provide a composition and a manufacturing method to meet these needs.

SUMMARY OF THE INVENTION

The present invention provides a composition and a method for the manufacturing of a mucoadhesive delivery system for the oral vaccination of animals. The mucoadhesive delivery vehicle releases the vaccine at the site of action (i.e., the Gut Associated Lymphoid Tissue; GALT) along the foregut and hindgut of the animal. In a preferred embodiment of the invention the mucoadhesive delivery vehicle is incorporated in the regular food or beverage normally consumed by the animal.

The mucoadhesive delivery vehicle is provided in a form of dry or semi-dry particles comprising an immunogenic substance (i.e., the vaccine), which is embedded in a composite matrix of cross-linked mucoadhesive polymer and protected by sugars.

It is an object of the invention to provide a manufacturing process of a mucoadhesive delivery vehicle for vaccination of animals and, in one embodiment, to aquatic animals.

Remarkably, the present inventors have found a way to produce large quantities of mucoadhesive particles containing vaccines with minimal drying efforts under sterile conditions and while using only food grade ingredients. In addition, when incorporated in a food product and administrated orally, the particles elicited both mucosal and systemic immune responses.

Thus, according to the present invention, there is provided a composition and a method of preparing a particle comprising a bioactive agent that is embedded in one or more mucoadhesive polymers, the one or more mucoadhesive polymer being further embedded in a glassy matrix, wherein the glassy matrix comprises: 10-60 wt % of sugars, 3-10 wt % of a oligosaccharides and 1-10 wt % of electrolytes, wherein the electrolytes, such as di- or poly-valent anion or cation compounds, act as cross-linking agents.

The present invention also provides a process of preparing a particle encapsulating a bioactive agent, the method comprising the steps of dissolving one or more mucoadhesive polymers in aqueous solution, admixing the bioactive agent under ambient temperature and slightly acidic conditions, extruding the slurry into a counter ion solution to form firm hydrogel beads or strings and saturating the hydrogel particles with sugars.

In additional embodiment, the sugar saturated hydrogel particles are further dehydrated by desiccation to reduce the moisture content to below 20%.

In one aspect the semi-dry particle materials are subjected to further drying and milling to obtain microparticulated powder containing the bioactive agent and having moisture content below 10%.

In another aspect, the present invention provides a semi-wet particle as described above, where the hydrogel particles are chopped for further size reduction without further drying.

In yet another aspect, the present invention provides a bioactive agent embedded in a mucoadhesive polymeric matrix and is further stabilized and thermo-protected by glassy matrix of sugars.

In still another aspect, the present invention provides a process of preparing a particle containing a bioactive agent where the hydrogel particles are saturated with sugars which significantly reduces the amount of free water in the particles and the associated need for extensive drying step.

In still another aspect, the present invention provides a process of preparing a particle containing a bioactive agent where all ingredients including salts and solutions are food grade ingredients, non-toxic, biodegradable and naturally occurring ingredients.

Yet another aspect of the present invention provides an immunogenic particle comprising a bioactive agent, one or more mucoadhesive polymer and an emulsifier all of which are cross-linked with a phosphate containing agent to form a hydrogel particle, and wherein the hydrogel particle is embedded in a sugar matrix.

The present invention has a number of unexpected advantages over the prior art. Thanks to the specific formulation and process conditions, the water content in the particles is very minimal while at the same time the formula also stabilizes the sensitive bioactive. A further important advantage is the excellent thermo-stability of the encapsulated ingredient. Without being bound by theory, it is believed that the amorphous sugar glassy structure created around the bioactive agent provides protection against the deleterious effects of heat and oxidation. This permits the particles of the present invention to be incorporated in a food product, the preparation of which entails pressure, sheer force, and heat treatments. Further advantages include the free-flowing characteristics of the particles of the invention as well as ability to control the particle size over a wide range from 5 microns to over 5000 micron.

DETAILED DESCRIPTION OF THE INVENTION

Definitions

Figure 1:
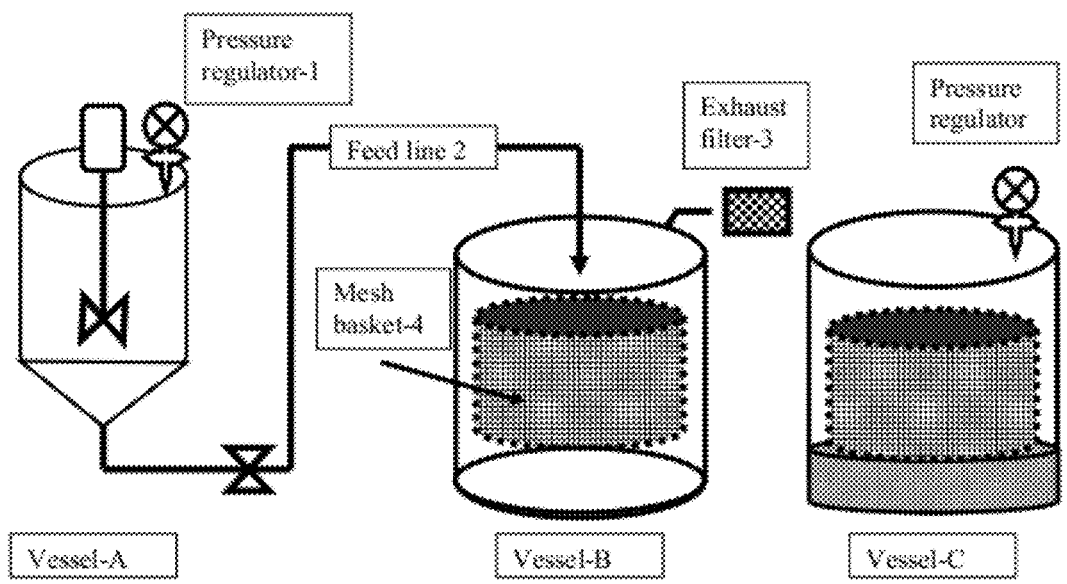
FIG. 1 shows a schematic side view of the apparatus for producing the particles of the current invention.

Unless otherwise defined herein, scientific and technical terminologies employed in the present disclosure shall have the meanings that are commonly understood and used by one of ordinary skill in the art. Also, as used herein and in the claims, the terms "at least one" and "one or more" have the same meaning and include one, two, three or more.

In describing the present invention, the following terminology is used in accordance with the definitions set out below.

"Bioactive Agent" refers to naturally occurring, synthetic, or semi-synthetic materials (e.g., compounds, fermentates, extracts, cellular structures) capable of eliciting, directly or indirectly, one or more physical, chemical, and/or biological effects. The bioactive agent may be capable of preventing, alleviating, treating, and/or curing abnormal and/or pathological conditions of a living body, such as by destroying a parasitic organism, or by limiting the effect of a disease or abnormality. Depending on the effect and/or its application, the bioactive agent may further be referred to as a pharmaceutical agent (such as an immunogen, a prophylactic agent, a therapeutic agent), a diagnostic agent, and/or a cosmetic agent, and includes, without limitation, vaccines, prodrugs, affinity molecules, synthetic organic molecules, polymers, low molecular weight molecules, proteinaceous compounds, peptides, vitamins, steroids, steroid analogs, lipids, nucleic acids, carbohydrates, precursors thereof, and derivatives thereof. The bioactive agent may also be a nutritional supplement. Non-limiting nutritional supplements include proteins, carbohydrates, water-soluble vitamins (e.g., vitamin C, B-complex vitamins, and the like), fat-soluble vitamins (e.g., vitamins A, D, E, K, and the like), and herbal extracts. The active agent may be commercially available and/or prepared by known techniques.

"Microencapsulation" is defined as a process that produces a composition containing a bioactive agent that is in the form of a microparticle in the size range of 10 to 5000 μm, or a composition that can be milled to a microparticle in the size range of 10 to 5000 μm.

"Complex" is defined as interaction between two molecules or portions of the same molecule through noncovalent interactions such as coordination bonds, electrostatic interactions, hydrogen bonding interactions, and hydrophobic interactions.

"Particle" refers to a particulate that is solid (including substantially solid or semi-solid, but excluding gel, liquid and gas), having an average geometric particle size (sometimes referred to as diameter) of less than 5 mm, preferably 500 microns or less, more preferably between 100 microns and 5 microns. Particles may be formed from, in part or in whole, with one or more non-limiting materials, such as the bioactive agents, mucoadhesive polymers, carriers, polymers, stabilizing agents, and/or complexing agents disclosed herein.

An "Immunogen" or an "Immunogenic Substance" is defined as a bioactive, a substance or a composition of matter, which is capable of mounting a specific immune response in an animal. Immunogenic substances would include immunogenic peptides and proteins including mixtures comprising immunogenic peptides and/or proteins (e.g., bacterins); intact inactive, attenuated, and infectious viral particles; intact killed, attenuated, and infectious prokaryotes; intact killed, attenuated, and infectious protozoans including any life cycle stage thereof, and intact killed, attenuated, and infectious multicellular pathogens, recombinant subunit vaccines, and recombinant vectors to deliver and express genes encoding Immunogenic proteins (e.g., DNA vaccines).

"Vaccination" is defined as a process that results in a specific immune response generated by an animal against an immunogen or an immunogenic substance.

A "Mucoadhesive Delivery System" or "Mucoadhesive Delivery Vehicle" is defined as a composition that results in the delivery of bioactive agent, an immunogen or an immunogenic substance to the desired location in the intestinal or nasal mucosa.

"Mucoadhesive Polymer" refers to a natural, synthetic, or semi-synthetic molecule having two or more repeating monomer units in a main chain or ring structure. Polymers broadly include dimers, trimers, tetramers, oligomers, higher molecular weight polymers, substituted derivatives thereof, and mixtures thereof. The polymer may be ionic or non-ionic, may be neutral, positively charged, negatively charged, or zwitterionic, and may be used singly or in combination of two or more thereof.

A "Mucoadhesive" molecule is a component of a mucoadhesive delivery system that specifically binds to mucosal tissues. Such molecules include, but are not limited to chitosan, alginate, hyloronic acid and cationic guar.

"Amorphous" refers to the glassy state of materials and constructions that lacking crystallinity or otherwise non-crystalline.

A "Glassy Matrix" for the purpose of the present invention, is an amorphous solid characterized by viscosities and an extremely low molecular mobility. The presence of a glassy state can be confirmed by establishing characteristic differential scanning calorimetry curves, for which particles are generally brought to the rubbery state by slow and continuous heating of the material.

"Semi-Dry or Semi-Wet" refers to a state that includes at least substantially solid and/or semi-solid, but excludes gel, liquid, and gas.

"Cross-Link," "Cross-Linked" and "Cross-Linking" generally refer to the linking of two or more materials and/or substances, including any of those disclosed herein, through one or more covalent and/or non-covalent (e.g., ionic) associations. Cross-linking may be effected naturally (e.g., disulfide bonds of cystine residues) or through synthetic or semi-synthetic routes. As described herein, cross-linking refer to converting polymeric slurry into a firm structure of hydrogel particles using salts having counter ions.

Oral administration of vaccines offers several advantages. Dosages can be administered to a large number of animals via the food or water with minimal labor and stress to the animal. Adverse immune reactions following oral administration are also much less likely to occur. For meat producing animals, oral administration has the additional advantage of avoiding common reactions or infections at injection site, broken needles, or the use of highly reactive adjuvant. These reactions decrease the value of the animal at harvest.

An effective oral delivery system requires a delicate balance among factors such as the simplicity of preparation, cost effectiveness, high loading level of the bioactive agent, controlled release ability, storage stability, and effective immunogenicity of the components. The method and process described herein offers significant advantages compared to other particulate delivery systems, including the conventional micro- and nano-encapsulation systems. It is also expected that the problems of instability, low loading level, and cost effectiveness are better resolved with the polymeric mucoadhesive system of the current invention.

The present invention provides a composition and a method for manufacturing of mucoadhesive particles containing one or more bioactive agents. Although various bioactive agents may be microencapsulated in accordance with this invention, the invention will be described below primarily with reference to the microencapsulation of Immunogenic Substances that are bacterin vaccines. Thus, according to one preferred embodiment, the present invention enables the oral delivery of an immunogenic vaccine useful in the prevention of disease in animals including aquatic animals.

Preparation of Bioadhesive Polymer slurry: a mucoadhesive polymer, such as but not limited to chitosan, at a concentration of 1-10% (w/w), is dispersed in 1-5 N acetic acid solution at a temperature in the range of 20° C. to 65° C. until fully dissolved. Indigestible short chain oligosaccharide components may be added to improve protection of the antigen from stomach acidity, bile acids, and proteases, and to increase the intestinal adsorption of the bioactive agent. Examples of materials that could be used include, but are not limited to, inulin and fructooligosaccharides (FOS). The pH of the slurry is then brought to about 5.8 and 0.5-10% (w/w) of a natural emulsifier such as lecithin is added to form a stable emulsion. One or more mono or disaccharides are then added to achieve a saturated emulsion with a concentration of from 5-50% (w/w). Without being bound by theory, it is believed that the emulsion is stabilized by the interaction between positive charge of the mucoadhesive polysaccharide, the emulsifier, and hydroxyl groups of the sugars and oligosaccharides. The increased hydrophobicity and elasticity of the mucoadhesive polysaccharide and emulsifier helps delay or prevent penetration of water or gastric juices into the matrix once formed into particles. In addition, the sugars and phospholipid complex increases the stability of the bioactive agent and protects the agent against heat. At the same time, the added sugars dramatically reduce the free water in the slurry, allowing for faster dehydration and drying. The pH of the slurry is then gradually increased to about pH 6.2 by the addition of base and a solution containing the bioactive agent added.

Hydrogel formation. Cross-linking is used to promote the formation of stable hydrogel particles. Various cross-linking agents have been used in fixing polymeric gels. These cross-linking agents are mostly synthetic chemicals such as formaldehyde, glutaraldehyde, dialdehyde, starch, glyceraldehydes, cyanamide, diimides, dimethyl adipimidate, diisocyanates, and epoxy compounds. However, these chemicals are all highly cytotoxic which will restrict their utility in food applications. Of these, glutaraldehyde is known to have allergenic properties and is cytotoxic at concentrations greater than 10-25 ppm and as low as 3 ppm in tissue culture. It is the purpose of this invention to provide a cross-linking agent suitable for use in food applications that is within acceptable cytotoxicity and that forms stable and biocompatible cross-linked products. To achieve this goal, a food grade product having a Generally Recognized As Safe (GRAS) status as a cross-linking agent (sodium triphosphate) has been used to form stable hydrogel particles. The resulting solution/suspension is then dropped or extruded into a cross-linking solution containing water-soluble phosphate salts. Upon contact, a salt exchange reaction (cross-linking) takes place, resulting in the formation of hydrogel beads or linear threads in which the bioactive agent is retained. The resulting suspension of particles containing the embedded bioactive agent is then soaked in a sugar saturated solution, collected, and dewatered to form semi-dry particles that can be further dried by a number of means well known in the art such as freeze drying, vacuum drying, spray drying, and the like, and milled to produce fine powder having a size range of from 5 to 5000 microns. Details of the manufacturing process are set out in the series of steps described below:

A solution comprising a bioactive agent such as, but not limited to, an immunogen or immunogenic substance(s) is dissolved into the slurry described above prior to cross-linking. The resulting composition is then allowed to fall in drops, or in a continuous stream, into a cross-linking solution of 1-10% sodium triphosphate solution. Alternatively, the slurry can be spray-atomized into an aqueous solution containing 1-10% sodium triphosphate. A chitosan/tripolyphosphate molecular mass ratio of at least about 4:1 is maintained. After a hardening period of 30-180 minutes, the wet particles beads or threads are harvested from the cross-linking bath by any suitable means well known in the art (e.g., screening, filtration, centrifugation, and the like) and soaked in a saturated sugar solution followed by mixing in any food acceptable desiccation compounds such as silica gel, starch granules and the like for further dewatering. The sodium triphosphate and the sugar saturated solutions can be reused for cross-linking more batches of chitosan slurry. The silica gel can also be washed, sterilized, and reused to dewater additional batches. The semi-dry particles are mixed in the feed formula for subsequent pelleting or extrusion. Alternatively, the semi-dry particles can be further dried using conventional processes well known in the art such as, but not limited to, freeze drying, vacuum drying, fluidized bed drying and tunnel drying. The dried material is then milled and sieved to the appropriate particle size class if necessary. The final sized particles can be mixed directly with the feed materials for subsequent pelleting or extrusion, or it can be mixed with edible oil for top-coating of a standard commercially available feed for oral administration.

Figure 2:
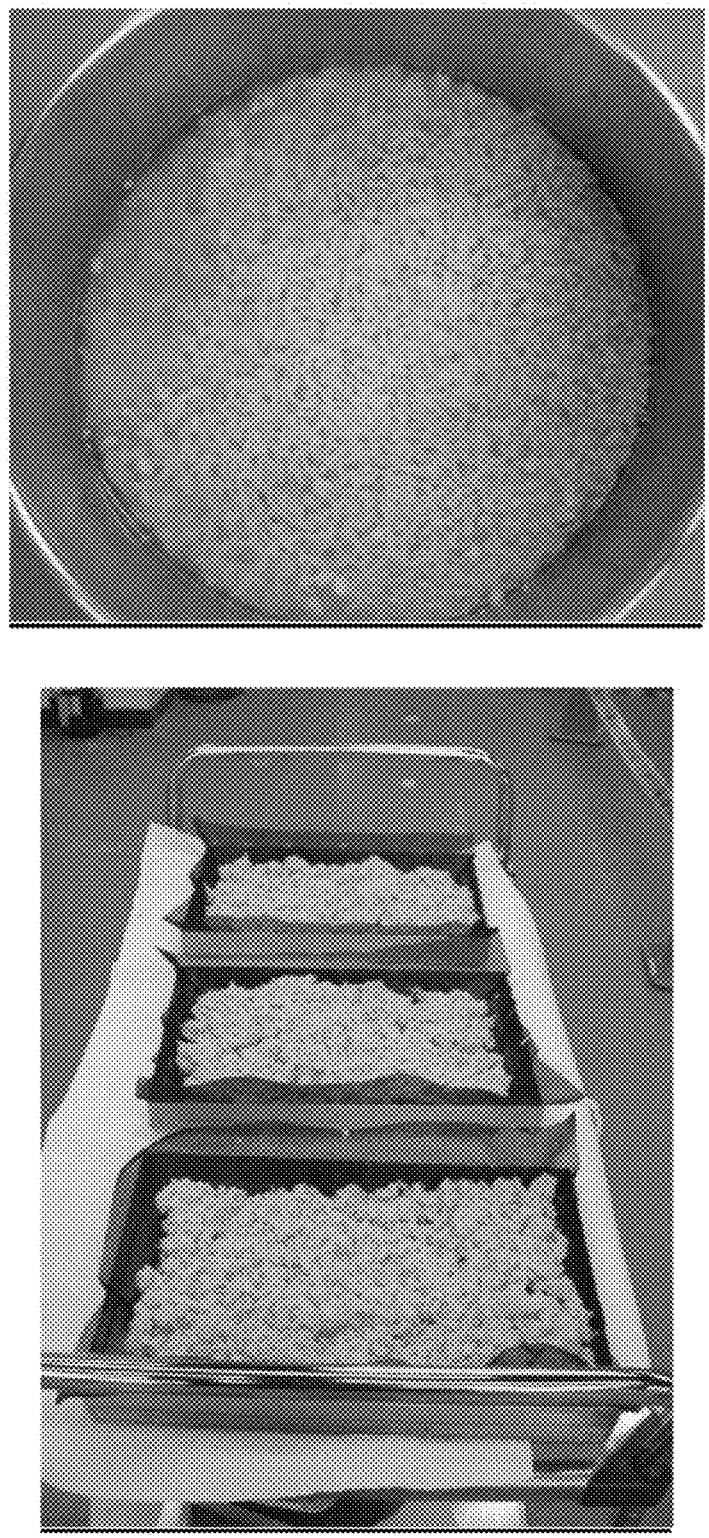
FIG. 2 shows the hydrogel strings before (upper picture) and after (bottom picture) harvesting from vessel B.

FIG. 1 demonstrates the process equipment which includes an airtight, stainless steel steam jacketed insulated mixing vessel (A) provided with a high-speed homogenizer from 250-20,000 RPM. The temperature in vessel-A is controlled from about 20° C. to 80° C. The mucoadhesive slurry containing the bioactive agent is prepared in vessel-A as described above. Nitrogen gas pressure from about 5-25 psi is then applied and controlled by Pressure regulator-1 to force the slurry through Feed line 2 (FIG. 1). The process tank (Vessel-B) is where the mucoadhesive polymer hydrogel beads or threads are formed. The airtight all stainless steel vessel is equipped with a liquid jet unit connected to Feed line-2, an exhaust system (Exhaust filter-3), and a removable stainless mesh basket (Mesh basket-4) that is raised about 10 cm from the vessel bottom. The liquid height in vessel-B is sufficient to maintain a minimum of 80 cm distance between the jet and the surface of the cross-linking solution in the tank which is necessary for allowing the stream of beads or continuous threads to settle at the bottom while hardening, thereby clearing the solution surface to accept freshly introduced material. In one embodiment of the present invention, the density of the slurry can be further adjusted by the addition of insoluble salts such as, but not limited, to calcium carbonate or calcium sulfate. This will allow for a rapid sinking of the beads or continuous threads to the tank bottom, thereby clearing the solution surface for freshly introduced material. Otherwise material may accumulate at the surface and prevent effective cross-linking of freshly introduced particles or threads. The hydrogel particles or threads are trapped within the mesh basket in vessel-B and are allowed to harden for 30-180 min. The Mesh basket-4 is then raised above the surface of the cross-linking solution and the beads or threads are allowed to drip dry for 30-120 min before being transferred to a third stainless steel vessel (Vessel-C) for further dewatering. FIG. 2 shows hydrogel strings before (upper picture) and after (bottom picture) harvesting from vessel B.

Vessel-C is similar to Vessel-B and serves for sugar soaking and dewatering of the hydrogel particles. Initially the tank filled with a solution containing at least 40% sugars or, more preferably, a sugar saturated solution. The hydrogel particles or threads are soaked in the sugar solution under vacuum of from about 1-100 mBARS for 30-60 min then allowed to drip dry by raising the mesh basket as described above. The sugar solution is removed from the tank and a thick layer of food compatible desiccating agent such as, but not limited to, silica gel beads or starch granules, is introduced to vessel-B. The mesh basket containing the hydrogel particles or threads is placed on top of the desiccating agent layer in vessel-C. A vacuum pressure from about 1-100 mBARS is applied again for additional 120 min. The semi-dry material containing 10-20% moisture is then removed from the vessel and chopped to smaller size and directly incorporated in a feed formula for pelleting or extrusion. Alternatively, the semi-dry material can be further dried to a moisture content of below about 10%, followed by milling and sieving through mesh screens of an appropriate size (e.g., from about 50-500 micron). The sodium triphosphate solution in Vessel-B and sugar saturated solution in Vessel-C can be reused for cross-linking more batches of chitosan slurry, and the silica gel in Vessel-C washed, sterilized, and reused to dewater additional batches.

The diameter of beads or strings produced by this method will vary depending on the jet diameter and stream velocity.

The jet diameter found to be useful in producing the particles was in the range from 50 to 7000 microns. The vertical jet velocity found to be useful was in the range of 0.1 cm³/sec to 10 cm³/sec. One of the advantages of the present invention is in the controlling of jet velocity by the nitrogen gas pressure applied in Vessel-A and the simple sterilization procedure which effectively eliminates the cumbersome use of a typical pumping system.

Additionally, in an alternative embodiment, the particles are removed from the mesh basket and directly placed in a drying unit without the dewatering step in Vessel-C. Due to the sugars saturation step, the hydrogel particles contain only about 30-40% water and thus require a minimal drying process to further reduce the moisture content to below 10%.

In another embodiment, the slurry is transferred from Vessel-A under a pressure of nitrogen gas to a separate pressure vessel connected to Feed line-2, and Vessel-C is used for sugar saturation while a separate similar Vessel-D is used for desiccation. This allows for continuous operation of the system, whereby additional chitosan/bioactive agent slurry is produced while Vessels-B, C and D are occupied with the formation and dewatering of the hydrogel particles or strings.

EXAMPLES

Example 1

Production of Mucoadhesive Polymer Particles

In a 400 L airtight steam jacketed stainless steel vessel, 180 L of sterile distilled water is added and warmed to 50° C. Three L of glacial acetic acid is carefully added (with mixing) to 17 liters of distilled water in an open flame hood. The diluted acetic acid solution is then slowly added to the distilled water in the steam jacketed stainless steel tank. Chitosan (4 kg high viscosity chitosan, Sigma, St. Louis, Mo.) is slowly added to the warmed acetic acid solution under a vigorous homogenizing (10,000 RPM) until completely dissolved. The chitosan solution is cooled to room temperature and the pH adjusted to 6.2 with 50% sodium hydroxide solution. Liquid soy lecithin (6 kg, Archer-Daniels-Midland Co., Decatur, Ill.) is added to the chitosan solution and the solution emulsified for 15 minutes under vigorous homogenization (10,000 RPM).

A solution of bacterin containing 5 million injectable doses is added to the chitosan slurry mixture prepared above. A pressure of 15 psi is then applied to the vessel and the slurry forced through ¼ quarter of inch feed line connected to a liquid jet head unit located at the center top cover of a 1000 L airtight steam jacketed stainless steel flat bottom vessel. The vessel is equipped with #10-12-mesh stainless steel basket located about 10 cm above the vessel bottom. The vessel contains 300 L of 10% w/w sodium triphosphate solution. The chitosan slurry is forced through a 5 mm liquid jet head unit that produces a uniform stream of the slurry into the sodium triphosphate solution. Uniform size strings of hydrogel are instantly formed and sink to the bottom of the meshed basket. The hydrogel strings are allowed to harden for 2 hours in the sodium triphosphate solution. After fully hardened, the meshed basket is raised above the solution surface and allowed to drip for an additional hour.

The mesh basket containing the hydrogel string material is then transferred to a similar 1000 L airtight stainless steel flat bottom vessel containing about 100 liter of sucrose saturated solution and a vacuum of 10 mBARS is applied for 30 minutes facilitating the absorption of the sugars by the hydrogel particles. The mesh basket is then raised above solution surface and the material is allowed to drip dry for 2 hours. The mesh basket containing the sugar saturated hydrogel material is then transferred to another similar 1000 litter airtight stainless steel flat bottom vessel containing about 100 kg of #35-60 mesh food grade and sterile silica gel. The vacuum on the tank is reduced to about 10 mBARS for 1 hour to provide further dewatering. The semi-dry hydrogel material containing about 20% moisture is chopped to small pieces of less than 1 mm in size for incorporation in a feed formula for pelleting or extrusion. Alternatively, the semi-dry hydrogel material can be further dehydrated to below 10% moisture in a vacuum drier or fluidized bed drier. Once the material attains a moisture content of less than 10%, it can be milled and sieved to provide final material of less than 100 micron particle size for incorporation in feed formula for pelleting or extrusion. This final sieved material can also be mixed in edible oil and used to top coat ready-made feed pellets.

Example 2

Production of Mucoadhesive Polymer Particles Using High Fructose Corn Syrup (HFCS)

Hydrogel Particles or strings are prepared as in Example 1. Sterile HFCS solution (Archer-Daniels-Midland Co., Decatur, Ill.) containing 55% fructose is used to saturate the hydrogel particles. 100 L of HFCS solution is added to a 1000 L airtight stainless steel flat bottom vessel and hydrogel particles are allowed to soak in the HFCS for about 30 minutes as described above in example 1. The particles are further dewatered in silica gel and semi-dry hydrogel material containing 20% moisture is obtained following the dehydration procedure described in example 1. The semi-dry hydrogel material is further dried in a fluidized bed drier at 50° C. to achieve a moisture level less than 10%. The resulting dried material is then milled using an industrial hammer mill and the powder is sieved to less than 100-microm-particle size.

Example 3

Production of Mucoadhesive Polymer Particles Containing Salmonid Rickettsial Septicaemia (SRS) Vaccine The mucoadhesive polymer slurry at pH 6.2 was prepared as described in Example 1. A solution containing attenuated SRS vaccine ($5 \times 10^{17}$/ml SRS bacterin) (commercially available from Centrovet, Santiago, Chile) was mixed with yeast extract immunostimulator (500 g beta glucan, AHD International, Atlanta, Ga.) and added into the slurry. The slurry was then injected into 10% w/v sodium triphosphate solution. The hydrogel material was allowed to harden for 2 hour and then saturated with sucrose. It was then further dewatered in silica gel, freeze dried, and milled to particle size lower than 100 micron.

Figure 3:
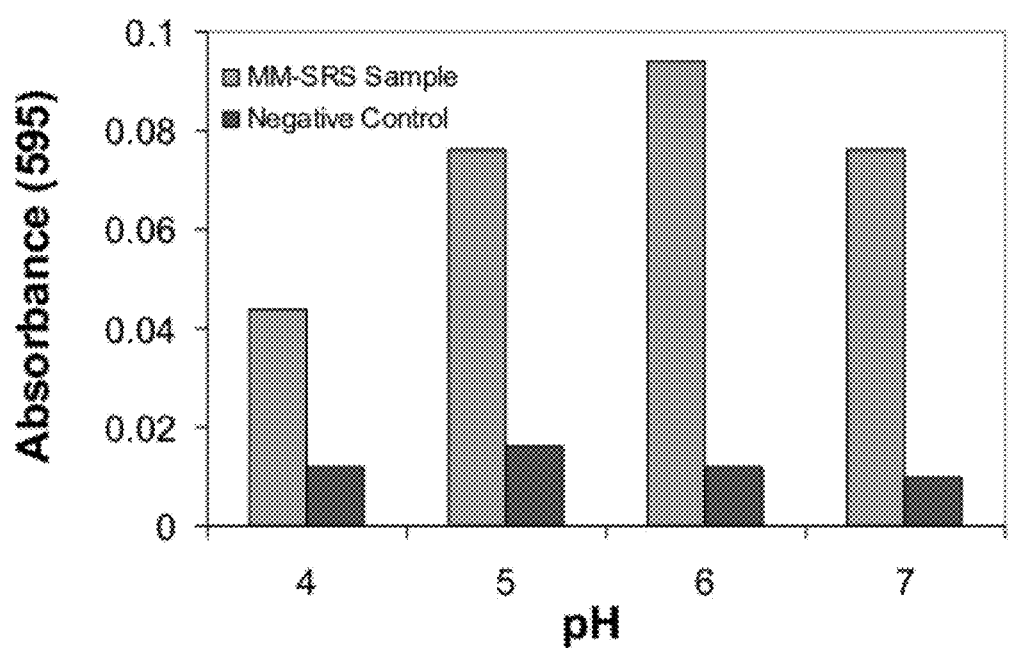
FIG. 3 shows the optimum treatment conditions for immunogen release from the particles.

An Enzyme-Linked ImmunoSorbant Assay (ELISA) was used to validate the presence of intact SRS vaccine in the mucoadhesive polymer particles. The encapsulated SRS vaccine produced above was homogenized in Phosphate-Buffered Saline (PBS) at different pH levels. FIG. 3 shows the optimum condition for immunogen release from the particles. This was followed by enzymatic treatment at 37° C. with continuous homogenization. The supernatant from the digested antigen preparation was used for ELISA and real-time Polymerase Chain Reaction (PCR) assay. Particles were homogenized and extracted in 10 mM PBS pH 6.3 containing chitosanase enzyme. Total protein was quantified using the Bradford microtiter assay (Bradford 1976). ELISA's were typical sandwich style in which the microtiter plates were coated with primary sheep antibody *P. salmonis* (Sigma). The SRS antibodies were captured overnight at 4° C., and the plate was reacted with a secondary anti-sheep IgG (Sigma HRP conjugate), followed by the anti-sheep alkaline phosphatase conjugate (Jackson Immunoresearch, West Grove, Pa.). The alkaline phosphatase is detected with para-nitrophenyl phosphate and read at 405 nm on a SpectroMax plate reader (Molecular Devices, Sunnyvale, Calif.).

Example 4

Production of Bioadhesive Particles with Enhanced Immunogenic Properties

In a 400 L airtight steam jacketed stainless steel vessel, 180 L of sterile distilled water is added and warmed to 50° C. Three L of glacial acetic acid is carefully added (with mixing) to 17 liters of distilled water in an open flame hood. The diluted acetic acid solution is then slowly added to the distilled water in the steam jacketed stainless steel tank. Chitosan (4 kg high viscosity chitosan, Sigma, St. Louis, Mo.) is slowly added to the warmed acetic acid solution under a vigorous homogenizing (10,000 RPM) until completely dissolved. The chitosan solution is cooled to room temperature and the pH adjusted to 6.2 with 50% sodium hydroxide solution. Instant Inulin (60 kg, Cargil, Minneapolis, Minn.) and liquid soy lecithin (6 kg, Archer-Daniels-Midland Co., Decatur, Ill.) are added to the chitosan solution and the solution emulsified for 15 minutes under vigorous homogenization (10,000 RPM). A solution containing 10 ml (equivalent to 5 million injectable doses) of attenuated bacterin vaccine, viral vaccine or yeast lysate containing proteins recombinants assembly in a VLP platform (available commercially from Novartis animal Health, Greensboro, N.C. USA.) are mixed with yeast extract immunostimulator (500 g beta glucan, AHD International, Atlanta, Ga.) and added into the chitosan slurry. The slurry is then injected into 10% w/v sodium triphosphate solution. The hydrogel material is allowed to harden for 2 hour and then saturated with sucrose. The hydrogel is further dewatered in Sharples centrifuge and dried in a freeze dryer. The resulting dried material is then milled using an industrial hammer mill and the powder is sieved to less than 100-microm-particle size.

Example 5

Production of Bioadhesive Particles Containing a Viral Antigen Vaccine Against Viral Infections in Fish The composition of the present invention is also effective in oral vaccination against viral infections such as infectious salmon anemia virus (ISAV), infectious pancreatic necrosis virus (IPNV), salmon swimbladder sarcoma virus (SSSV), etc. One injectable dose may be equivalent to 2-20 micro liter solution of attenuated virus vaccine or yeast lysate containing recombinant proteins obtained from sequences of isolated virus. Both types of vaccines are available commercially from Centrovet, Santiago, Chile or Novartis animal Health, Greensboro, N.C. USA. A typical formulation involves the preparation of slurry as described in Example 1. A solution containing 5 million doses of attenuated virus or proteins recombinants are mixed with yeast extract immunostimulator (500 g beta glucan, AHD International, Atlanta, Ga.) and added into the slurry. The slurry is then injected into 10% w/v sodium triphosphate solution. The hydrogel material is allowed to harden for 2 hour and then saturated with sucrose. It is then further dewatered in silica gel or Sharples centrifuge, freeze dried, vacuum dried or fluidized bed dried, and milled to particle size lower than 100 micron.

Example 6

Production of Bioadhesive Particles Containing a Viral Antigen Vaccine Against ISAV A 10 ml of yeast lysate solution (equivalent to 5 million injectable doses) containing proteins recombinants obtained from sequences of isolated virus of a Chilean origin (available commercially from Centrovet, Santiago, Chile) is mixed with yeast extract immunostimulator (500 g beta glucan, AHD International, Atlanta, Ga.) and added into a slurry as described in example 1. The slurry is then injected into 10% w/v sodium triphosphate solution. The hydrogel material is allowed to harden for 2 hour and then saturated with sucrose. The hydrogel is further dewatered in Sharples centrifuge and dried in a freeze dryer. The dried material is milled to particle size lower than 100 micron.

Example 7

Production of Bioadhesive Particles Containing a Viral Antigen Vaccine Against IPNV The economical loss due to IPN is significant in the salmon farming industry, and outbreaks may occur both in fresh water pre-smolt and post-smolt salmon after transferred to sea-water. An IPNV infection may persist without any signs of disease, but it may reactivate with new outbreaks in post-smolts after transfer to seawater. Effective injectable vaccines are available, but difficult to apply in small early pre-smolt salmon juveniles. An oral application using virus-like particle (VLP) as a platform and the formulation of the current invention is produced. A 10 ml of yeast lysate solution (equivalent to 5 million injectable doses) containing proteins recombinants assembly in a VLP platform (available commercially from Novartis animal Health, Greensboro, N.C. USA.) is mixed with yeast extract immunostimulator (500 g beta glucan, AHD International, Atlanta, Ga.) and added into a slurry as described in example 1. The slurry is then injected into 10% w/v sodium triphosphate solution. The hydrogel material is allowed to harden for 2 hour and then saturated with sucrose. The hydrogel is further dewatered in Sharples centrifuge and dried in a freeze dryer. The resulting dried material is then milled using an industrial hammer mill and the powder is sieved to less than 100-microm-particle size.

Example 8

Production of Storage Stable Bioadhesive Particles Containing a Viral Antigen Vaccine Against Viral Infections in Fish The final drying step of the composition of the present invention may be carried out in a way that allowed the formation of a sugar glass matrix surrounded the vaccine particles. Such a glassy formation stabilizes and protects the vaccine under unfavorable storage conditions of high temperature and humidity. Oral bacterin vaccines against a bacterial disease such as an SRS or viral vaccines against virus infections such as ISAV or IPNV were prepared as described in Example 6 or 7 and the final drying step of the sugar loaded thin threads or strings were dried in such a way that a sugar glass is formed. The thin threads were loaded on a 13×10" tray (13×10 inch) at a loading capacity of 800 g/sq ft and placed in a freeze drier (Virtis Advantage, Virtis, Gardiner, N.Y.). The Condenser is chilled to −50° C., shelf temperature was adjusted to 40° degree C. and the material allowed to warm up to about 35° C. (measured by a pair of temperature sensors plugged in the wet material). Vacuum was then initiated and controlled at about 2500 mTORR through an external vacuum controller, (Thyr-Cont, Electronic, GmbH). As vacuum pulled down the product temperature fall and stabilized at about ±2° C. After 16 hours, the product temperature had increased to about +10° C. At this point, a full vacuum pressure was applied and shelf temperature rose to 50° C. Twelve hours after establishing full vacuum pressure, the dried product was taken out of the freeze drier and milled to particle size lower than 100 micron.

Example 9

Production of Atlantic Salmon Feed Containing SRS Immunogenic Microparticles

Fifteen kg of dry powder of SRS immunogenic microparticles was prepared as in Example 3 and mixed with 30 kg of fish oil. The oily mixture was sprayed on 1000 kg of standard commercial feed for Atlantic salmon juveniles (Ewos, Km 20 Coronel, Concepción, Chile) and the oral vaccination feed was stored in 4° C. during its use.

Example 10

Production of Mucoadhesive Polymer Particles Containing *Mycoplasma hyopneumoniae* (M. hyo) Vaccine

*Mycoplasma hyopneumoniae* (M. hyo) is a widespread pathogen, found in swine herds throughout the world. The organism is associated with the development of bronchopneumonia. The disease leads to severe productivity losses by way of reduced weight gain and poor food conversion rates in the growing pigs. To orally vaccinate the pig, the slurry (pH 6.2) was prepared as described in Example 2. A solution containing 5 million doses of attenuated M. hyo vaccine commercially available from Boehringer Ingelheim Limited, Berkshire UK. is mixed with 500 g yeast extract immunostimulator (pure beta glucan, AHD International, Atlanta, Ga.) and added into the slurry. The slurry is then injected into 10% w/v sodium triphosphate solution containing HFCS. The hydrogel material is allowed to harden for 2 hour and then further dewatered and chopped to a particle size less than 1 mm and kept refrigerated until incorporated in feed formula for pellet extrusion.

Example 11

Oral Vaccination of Pigs Against M. hyo Using the Immunogenic Microparticles of the Present Invention Semi-dry immunogenic particles produced as described in example 10 are incorporated in standard feed formula for growing pigs and a pelleted feed is produced. Growing pigs are fed once a day with a diet containing 1 dose of the injectable vaccine for a total of 5 days. Growth performances of vaccinated and non-vaccinated pigs are recorded.

Example 12

Nasal Vaccination of Pigs Against M. hyo Using the Immunogenic Microparticles of the Present Invention The semi-dry hydrogel particles produced as described in examples 2 and 10 are dried in a vacuum drier to further reduce the moisture content to below 10%. The dry material is milled using an industrial hammer mill and sieved to particle size less than 30 micron. Growing pigs are immunized with the immunogenic microparticles via the respiratory tract and growth performances of vaccinated and non-vaccinated pigs recorded.

REFERENCES

The contents of all references cited herein are hereby incorporated by reference herein for all purposes.

Aral, C. and Akbuga, A, J. (1998). Alternative approach to the preparation of chitosan beads. *International of Journal of Pharmaceutics*, 168:9-15.

Bradford, M. M. (1976). A rapid and sensitive method for the quantitation of microgram quantities of protein utilizing the principal of protein-dye binding. *Anal. Biochem.* 72:248-254.

Bodmeier, R., Oh, K. H. and Pramar, Y. (1989). Preparation and evaluation of drug containing chitosan beads. *Drug Development and Industrial Pharmacy*, 15, 1475-1494.

Calvo, P., Remun, A., N-Lopez, C., Vila-Jato, J. L. and Alonso, M. J. (1997). Novel hydrophilic chitosan-polyethylene oxide nanoparticles as protein carriers. *Journal of Applied Polymer Science*, 63: 125-132.

Chopra, S., S. Mandi, et al. (2006). "Advances and potential applications of chitosan derivatives as mucoadhesive biomaterials in modern drug delivery." *J. Pharm. Pharmacol.* 58(8): 1021-1032.

Dang, J. M. and K. W. Leong (2006). "Natural polymers for gene delivery and tissue engineering." *Adv. Drug Deliv. Rev.* 58(4): 487-499.

Davis, S. S. (2006). "The use of soluble polymers and polymer microparticles to provide improved vaccine responses after parenteral and mucosal delivery." *Vaccine* 24(2): 7-10.

Huang, Y. C., Chiang, C. H. and Yeh, M. K. (2003), Optimizing Formulation Factors in Preparing Chitosan Microparticles by Spray-drying Method, *Journal of Microencapsulation*, 20(2: 247-260.

Kang, M. L., H. L. Jiang, et al. (2007). "Pluronic F127 enhances the effect as an adjuvant of chitosan microspheres in the intranasal delivery of *Bordetella bronchiseptica* antigens containing dermonecrotoxin." *Vaccine* 25(23): 4602-4610.

Kim, T. J., K. H. Kim, et al. (2007). "Stimulation of mucosal and systemic antibody responses against recombinant transferrin-binding protein B of *Actinobacillus pleuropneumoniae* with chitosan after tracheal administration in piglets." *J. Vet. Med. Sci.* 69(5): 535-539.

Malik, D. K., S. Baboota, et al. (2007). "Recent advances in protein and peptide drug delivery systems." *Curr. Drug Deliv.* 4(2): 141-151.

Rege P. R, Gramise R. J, Block L. H. (2003). Spray-dried chitinosans. Part-I: preparation and characterization. *Int J Pharm.* 252:41-51.

Shiraishi, S., Imai, T. and Otagiri, M. (1993). Controlled release of indomethacin by chitosan-polyelectrolyte complex: optimization and in vivo/in vitro evaluation. *Journal of Controlled Release*, 25: 217-225.

Shu, X. Z. and Zhu, K. J., (2000). A novel approach to prepare tripolyphosphate/chitosan complex beads for controlled drug delivery. International of Journal of Pharmaceutics, 201, 51-58.

van der Lubben, I. M., J. C. Verhoef, et al. (2001). "Chitosan for mucosal vaccination." *Advanced Drug Delivery Reviews* 52 (2): 139-144.

van der Lubben, I. M., J. C. Verhoef, et al. (2001). "Chitosan microparticles for oral vaccination: preparation, characterization and preliminary in vivo uptake studies in murine Peyer's patches." *Biomaterials* 22(7): 687-694.

That which is claimed is:

1. A method of preparing an immunogenic substance suitable for oral or nasal vaccination, wherein the immunogenic substance consists of a vaccine, a crosslinked mucoadhesive polymer, one or more sugars, one or more oligosaccharides and one or more electrolytes,
   wherein the one or more sugars are selected from the group consisting of fructose, sucrose, dextrose, and trehalose,
   wherein the one or more oligosaccharides are selected from the group consisting of inulin and frutcoologosaccharides (FOS), and
   wherein the mucoadhesive polymer is a polymer that is not a dimer,
   the method comprising:
   (a) dissolving a mucoadhesive polymer and the one or more oligosaccharides in an aqueous solution;
   (b) mixing the vaccine with the resulting solution from step (a) to form a slurry;
   (c) cross-linking the mucoadhesive polymer in the slurry with the one or more electrolytes to form hydrogel particles;
   (d) soaking the hydrogel particles in a solution saturated with one or more sugars to make semi-dry particles; and
   (e) drying the semi-dry particles, whereby the immunogenic substance is formed.

2. The method of claim 1, wherein the vaccine is a bacterin vaccine, a viral vaccine, or a recombinant vector that expresses a gene encoding an immunogenic protein.

3. The method of claim 1, wherein the mucoadhesive polymer is a polysaccharide.

4. The method of claim 3, wherein the polysaccharide is selected from the group consisting of chitosan, hyaluronic acid, alginate, cationic guar, and derivatives thereof.

5. The method of claim 1, wherein the sugar is a monosaccharide or a disaccharide.

6. The method of claim 5, wherein the disaccharide is selected from the group consisting of sucrose and trehalose.

7. The method of claim 1, wherein the one or more electrolytes are one or more divalent or polyvalent cations or anions.

8. The method of claim 1, wherein the one or more electrolytes are one or more salts of Ca, Zn, Al, triphosphate or hexametaphosphate.

9. The method of claim 1, wherein the vaccine is selected from the group consisting of (a) recombinant vectors containing a gene encoding an immunogenic protein, (b) intact inactive, attenuated and infectious viral particles, (c) intact killed, attenuated and infectious prokaryotes, (d) intact killed, attenuated and infectious protozoans, and (e) intact killed, attenuated and infectious multicellular pathogens.

10. The method of claim 1, wherein the vaccine is against infectious salmon anemia virus (ISAV), Salmonid Rickettsial Septicaemia (SRS) or infectious pancreatic necrosis virus (IPNV).

11. The method of claim 1, further comprising blending the immunogenic substance with oil and top-coating feed pellets.

12. The method of claim 11, further comprising spray coating the immunogenic substance on the feed pellets.

13. The method of claim 1, further comprising:
    (f) incorporating the immunogenic substance into a feed formula, and
    (g) pelleting or extruding the resulting feed formula from step (f), whereby a dry feed pellet containing the immunogenic substance is formed.

14. The method of claim 1, wherein the vaccination is oral.

15. The method of claim 1, wherein the vaccination is nasal.

16. The method of claim 1, further comprising freeze drying or spray drying the immunogenic substance, whereby a dry immunogenic powder is formed.

17. The method of claim 1, wherein the semi-dry particles have a moisture content of 10-20%.

18. The method of claim 1, wherein the mucoadhesive polymer is chitosan and the one or more electrolytes contain a soluble phosphate salt.

19. The method of claim 1, wherein the mucoadhesive polymer is alginate and the one or more electrolytes contain a soluble calcium salt.

20. The method of claim 1, wherein the immunogenic substance contains the one or more sugars at 10-60 wt %, the one or more oligosaccharides at 3-10 wt %, and the one or more electrolytes at 1-10 wt %.

21. A method of preparing an immunogenic substance suitable for oral or nasal vaccination,
    wherein the immunogenic substance consists of a vaccine, a cross-linked mucoadhesive polymer, one or more sugars, one or more oligosaccharides, one or more electrolytes, and an additional agent selected from the group consisting of a phospholipid, beta glucan and a combination thereof,
    wherein the one or more sugars are selected from the group consisting of fructose, sucrose, dextrose, and trehalose,
    wherein the one or more oligosaccharides are selected from the group consisting of inulin and fructooligosaccharides (FOS), and
    wherein the mucoadhesive polymer is a polymer that is not a dimer,
    the method comprising:
    (a) dissolving a mucoadhesive polymer and the one or more oligosaccharides in an aqueous solution;
    (b) mixing the vaccine with the resulting solution from step (a) to form a slurry;
    (c) adding the additional agent to the aqueous solution of step (a) or the slurry of step (b);
    (d) cross-linking the mucoadhesive polymer in the slurry with the one or more electrolytes to form hydrogel particles;
    (e) soaking the hydrogel particles in a solution saturated with one or more sugars to make semi-dry particles; and (f) drying the semi-dry particles, whereby the immunogenic substance is formed.

22. The method of claim 21, wherein the additional agent is a phospholipid, wherein the phospholipid is lecithin.

\* \* \* \* \*